United States Patent
Phillips et al.

(10) Patent No.: US 7,671,178 B1
(45) Date of Patent: Mar. 2, 2010

(54) SOLUBILIZATION AND RECONSTITUTION OF SILK USING IONIC LIQUIDS

(75) Inventors: David M. Phillips, Huber Heights, OH (US); Robert A. Mantz, Dayton, OH (US); Paul C. Trulove, Annapolis, MD (US); Hugh C. DeLong, Waldorf, MD (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 11/326,678

(22) Filed: Dec. 29, 2005

Related U.S. Application Data

(60) Provisional application No. 60/640,559, filed on Dec. 30, 2004.

(51) Int. Cl.
*C07K 14/00* (2006.01)
(52) U.S. Cl. .................................. 530/353; 530/350
(58) Field of Classification Search ................ 530/353, 530/350
See application file for complete search history.

(56) References Cited

U.S. PATENT DOCUMENTS 5,252,285 A * 10/1993 Lock .......................... 264/202
2003/0157351 A1 * 8/2003 Swatloski et al. ........ 428/478.4

OTHER PUBLICATIONS

Phillips et al., Dissolution and Regeneration of Bombyx mori Silk Fibroin Uisng Ionic Liquids, J. Am. Chem. Soc. 2004, 126, 14350-14351.*
Swatloski et al., Dissolution of Cellulose with Ionic Liquids, J. Am. Chem. Soc. 2002, 124, pp. 4974-4975.*

* cited by examiner

*Primary Examiner*—Chih-Min Kam
(74) *Attorney, Agent, or Firm*—AFMCLO/JAZ; Bart S. Hersko

(57) ABSTRACT

Silk is dissolved in an ionic liquid and is regenerated in a range of structural forms without requiring the use of harmful solvents. Silk solubility can be controlled by the selection of the ionic liquid constituents, with small cations and halide or pseudohalide anions favoring solution. The rinse solvent exercises a significant influence over the final properties of the regenerated silk.

18 Claims, 3 Drawing Sheets

SOLUBILIZATION AND RECONSTITUTION OF SILK USING IONIC LIQUIDS

This application claims benefit of U.S. Provisional Patent Application Ser. No. 60/640,559, filed on Dec. 30, 2004.

RIGHTS OF THE GOVERNMENT

The invention described herein may be manufactured and used by or for the Government of the United States for all governmental purposes without the payment of any royalty.

BACKGROUND OF THE INVENTION

The invention relates to the dissolution and regeneration of silk and silk-like proteins in ionic liquids.

Natural silk fibers from arthropods have outstanding mechanical properties that rival the most advanced synthetic polymers. Compared to the limited number of molecular solvents available today, ionic liquids have taken the spotlight as green, designer solvents, with many combinations that offer an unprecedented versatility and tunability. In this invention, we demonstrate the suitability of ionic liquids for dissolving and regenerating silk and examine the solution properties and the structural properties of regenerated silk films cast from ionic liquid solutions.

The use of arthropod silk throughout its 5000 year history has been primarily limited to its natural form of fibers. To expand the use of silk as a material for other applications, it is desirable to develop alternative processing methodologies. Some of the possibilities for silk with alternative processing include customized fiber deniers; thicker, monofilament fibers for medical sutures; scaffolds for tissue regeneration and cell growth; and films.

A single strand of natural cocoon silk fiber from the silkworm *Bombyx mori* contains two silk fibroin cores surrounded by a protective, glue-like sericin coating. The sericin must be removed from a cocoon before the single strand of silk comprising the cocoon can be collected as a continuous fiber. The actual fibroin cores consist of two macromolecules, with molecular weights of 391 kDa and 26 kDa for the heavy and light chains, respectively. The sequence of the heavy chain is repetitive and semi-crystalline, while the sequence of the light chain is non-repetitive and non-crystalline.

The crystalline regions of the heavy chain occur primarily in the repeated amino acid motifs. These regions form a hydrogen bonded, anti-parallel, β-sheet structure in the natural cocoon fiber. The hydrogen bonding and the hydrophobic nature of these crystalline regions make dissolution of silk a formidable task.

Multiple methods have been utilized to prepare silk fibroin solutions. These generally involve stripping the sericin in a soap solution, $Na_2CO_3$ wash, enzymatic solution of alkalase, or a urea wash; rinsing and drying the silk; and dissolving the silk in a high concentration, aqueous lithium salt solution or a $CaCl_2$/ethanol/water solution. [See e.g., Yamada, H.; Nakao, H.; Takasu, Y.; Tsubouchi, K., *Mat. Sci. Eng. C* 2001, 14, 41-46] These solutions are subsequently dialyzed into water to remove the salt and have a shelf life of about 1 week before the onset of gelation. Stable fibroin solutions can be prepared by lyophilizing the dialyzed solutions or casting films of silk and dissolving the resulting silk in another solvent, such as 1,1,1,3,3,3-hexafluoro-2-propanol, hexafluoroacetone, or trifluoroacetic acid. All of these solvents are toxic and are gaseous or volatile at standard temperature and pressure.

It has now been found that silk can be dissolved in solvents that are described as ionic liquids. These ionic liquids typically have a melting point below 150° C. and consist of cations and anions. It has also been found that a wide and varied range of ionic liquids can be used to provide greater control and flexibility in the overall processing methodology. It has further been found that silk-containing materials can be regenerated from an ionic liquid solvent system without using other undesirable solvents in the process. These findings are discussed in the disclosure that follows.

SUMMARY OF THE INVENTION

A method for dissolving silk is disclosed herein. That method comprises admixing silk and silk-like proteins with a hydrophilic ionic liquid comprised of cations. The admixture is agitated until dissolution is complete. The admixture is heated in some embodiments, including conduction and/or radiating with microwaves. The ionic liquid is molten at a temperature less than about 150° C. Although not required, cosolvents, such as water, can be combined with the ionic liquids to modify dissolution.

The cations of an ionic liquid are preferably cyclic and correspond in structure to a formula selected from the group consisting of

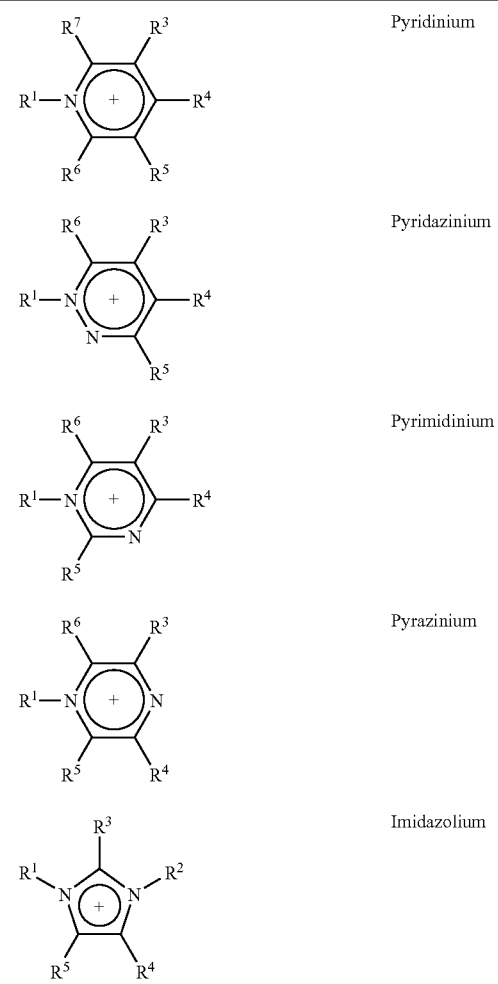

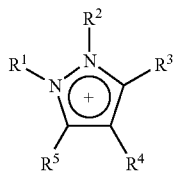 Pyrazolium

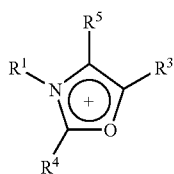 Oxazolium

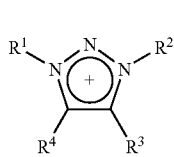 1,2,3-triazolium

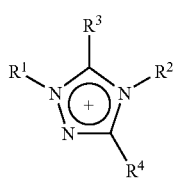 1,2,3-triazolium

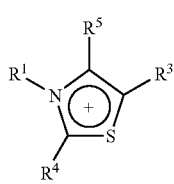 Thiazolium

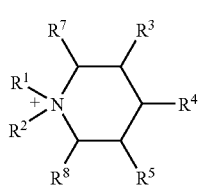 Piperidinium

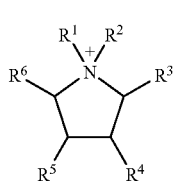 Pyrrolidinium

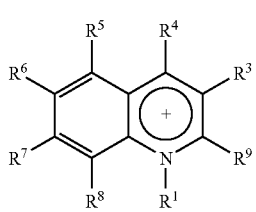 Quinolinium

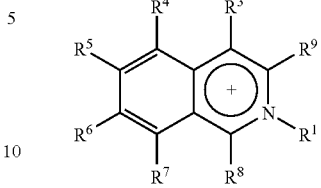 Isoquinolinium wherein $R^1$ and $R^2$ are independently a $C_1$-$C_6$ alkyl group or a $C_1$-$C_6$ alkoxyalkyl group, and $R^3$, $R^4$, $R^5$, $R^6$, $R^7$, $R^8$ and $R^9$ ($R^3$-$R^9$), when present, are independently a hydrido, a $C_1$-$C_6$ alkyl, a $C_1$-$C_6$ alkoxyalkyl group, or a $C_1$-$C_6$ alkoxy group. The anions of the ionic liquid are halogen, pseudohalogen, or $C_1$-$C_6$ carboxylate. It is to be noted that there are two iosmeric 1,2,3-triazoles. It is preferred that all R groups not required for cation formation be hydrido.

A cation that contains a single five-membered ring that is free of fusion to other ring structures is more preferred. A silk dissolution method is also disclosed herein using an ionic liquid comprised of those cations. That method comprises admixing silk with a hydrophilic ionic liquid comprised of those five-membered ring cations and anions to form an admixture. The admixture is agitated until dissolution is complete. Exemplary cations are illustrated below wherein $R^1$, $R^2$, and $R^3$-$R^5$, when present, are as defined before.

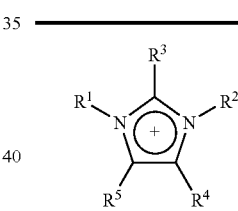 Imidazolium

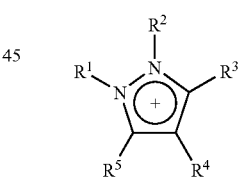 Pyrazolium

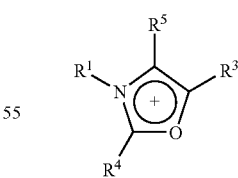 Oxazolium

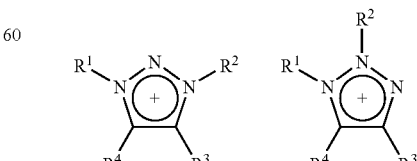 1,2,3-triazolium

-continued

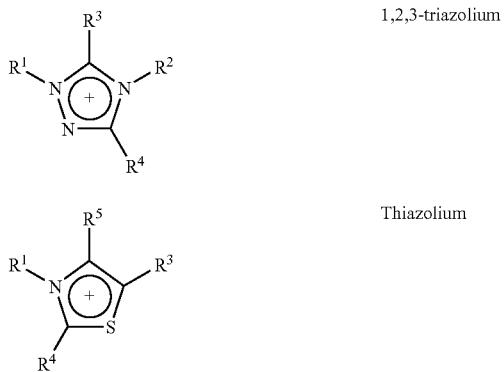

1,2,3-triazolium

Thiazolium

Of the more preferred cations that contain a single five-membered ring free of fusion to other ring structures, an imidazolium cation that corresponds in structure to Formula A is particularly preferred, wherein $R^1$, $R^2$, and $R^3$-$R^5$, are as defined before.

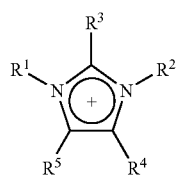

A 1,3-di-($C_1$-$C_6$ alkyl)-substituted-imidazolium and 1,2,3-tri-($C_1$-$C_6$ alkyl)-substituted-imidazolium ions are more particularly preferred cations; i.e., an imidazolium cation wherein $R^4$-$R^5$ of Formula A are each hydrido, $R^3$ is either a hydrido or a $C_1$-$C_6$-alkyl group or a $C_1$-$C_6$ alkoxyalkyl group, and $R^1$ and $R^2$ are independently each a $C_1$-$C_6$-alkyl group or a $C_1$-$C_6$ alkoxyalkyl group. A 1-($C_1$-$C_6$-alkyl)-3-(methyl)-imidazolium [$C_n$-mim, where n=1-6] cation is most preferred, and a halogen is a preferred anion. A most preferred cation is illustrated by a compound that corresponds in structure to Formula B, below, wherein $R^4$-$R^5$ of Formula A are each hydrido and $R^1$ and $R^3$ are each a $C_1$-$C_6$-alkyl group or a $C_1$-$C_6$ alkoxyalkyl group.

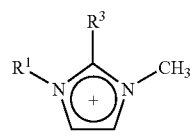

B

A method for regenerating silk is also disclosed herein. That method comprises admixing a solution of silk in a molten hydrophilic ionic liquid solvent or in a hydrophilic ionic liquid whose cations contain a single five-membered ring free of fusion to other ring structures with a nonsolvent for the silk that is miscible with the ionic liquid. The admixing leeches the ionic liquid from the silk to form separate phases for the silk and ionic liquid, respectively. The regenerated silk is preferably collected as a solid phase. The ionic liquids used in this method are those discussed above.

DETAILED DESCRIPTION

Figure 1A:
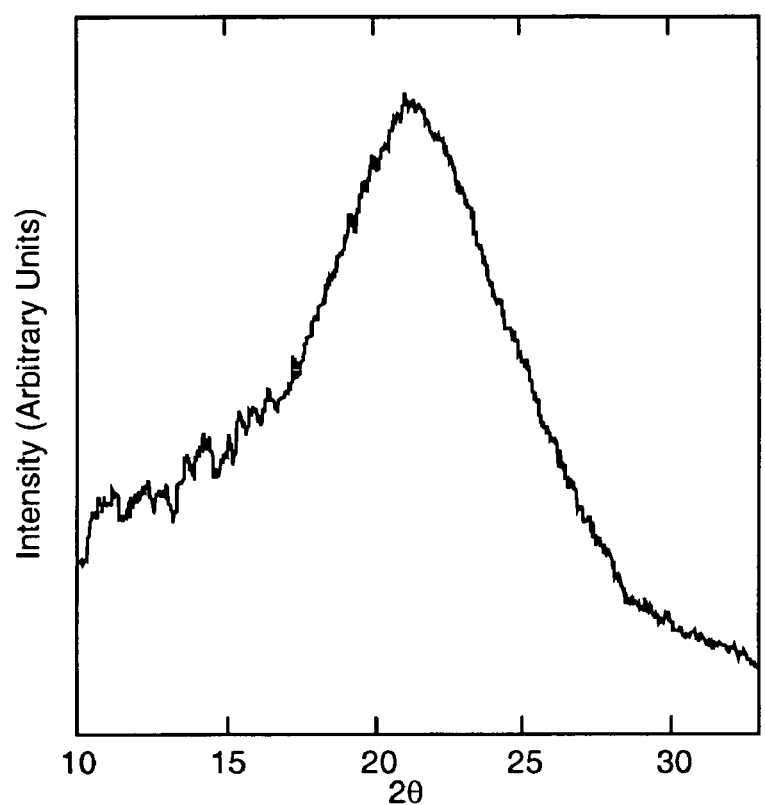
FIGS. 1a and 1b show the wide angle X-ray scattering (WAXS) crystallinity analysis of for (a) 12.24% (w/w) silk in [$C_4$mim]Cl at 30° C. and (b) pure [$C_4$mim]Cl at 30° C.

The present invention relates to the formation of silk and silk-like protein solutions in ionic liquids for the purpose of silk regeneration. The solvent is an ionic liquid, comprising an organic cation and an inorganic or organic anion. Although not required, cosolvents, such as water, can be combined with the ionic liquids to modify dissolution.

A method for dissolving silk is disclosed herein. That method comprises admixing silk and silk-like proteins with a hydrophilic ionic liquid comprised of cations. The admixture is agitated until dissolution is complete. The admixture is heated by conduction, convection, and/or radiation, including by exposure to microwaves. The ionic liquid is molten at a temperature less than about 150° C.

An exemplary cyclic ionic liquid cation corresponds in structure to a formula shown below:

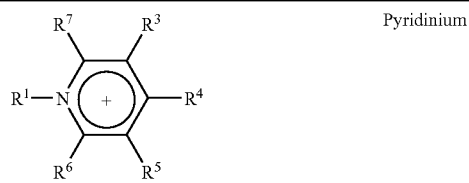

Pyridinium

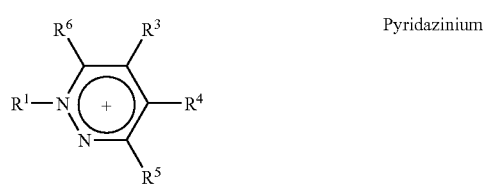

Pyridazinium

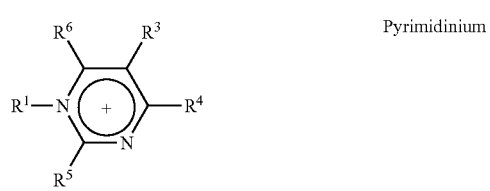

Pyrimidinium

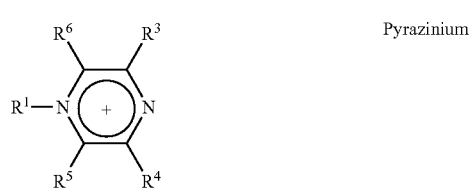

Pyrazinium

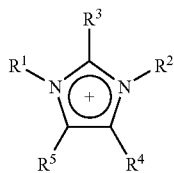 Imidazolium

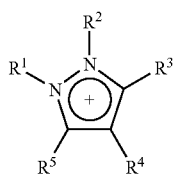 Pyrazolium

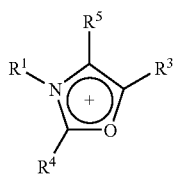 Oxazolium

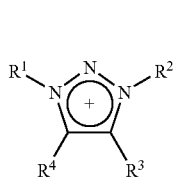 1,2,3-triazolium

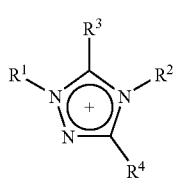 1,2,3-triazolium

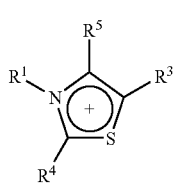 Thiazolium

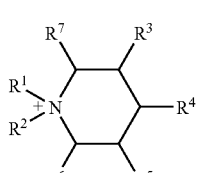 Piperidinium

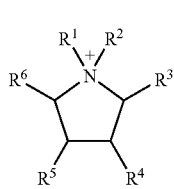 Pyrrolidinium

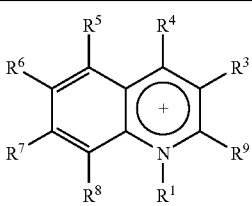 Quinolinium

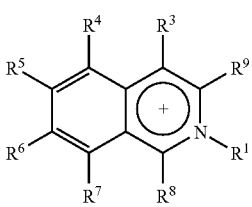 Isoquinolinium wherein $R^1$ and $R^2$ are independently a $C_1$-$C_6$ alkyl group or a $C_1$-$C_6$ alkoxyalkyl group, and $R^3$, $R^4$, $R^5$, $R^6$, $R^7$, $R^8$ and $R^9$ ($R^3$-$R^9$), when present, are independently a hydrido, a $C_1$-$C_6$ alkyl, a $C_1$-$C_6$ alkoxyalkyl group or a $C_1$-$C_6$ alkoxy group. More preferably, both $R^1$ and $R^2$ groups are $C_1$-$C_4$ alkyl, with one being methyl, $R^3$ is a methyl or hydrido, and $R^4$-$R^9$, when present, are preferably hydrido. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl and the like. Corresponding $C_1$-$C_6$ alkoxy groups contain the above $C_1$-$C_6$ alkyl group bonded to an oxygen atom that is also bonded to the cation ring. An alkoxyalkyl group contains an ether group bonded to an alkyl group, and here contains a total of up to six carbon atoms.

The phrase "when present" is often used herein in regard to substituent R group because not all cations have all of the numbered groups. All of the cations contain at least four R groups, although $R^2$ need not be present in all cations.

An anion for a ionic liquid cation is preferably a halogen ion (fluoride, chloride, bromide, or iodide), perchlorate, a pseudohalogen ion such as thiocyanate and cyanate or $C_1$-$C_6$ carboxylate. Pseudohalides are monovalent and have properties similar to those of halides [Schriver et al., Inorganic Chemistry, W. H. Freeman & Co., New York (1990) 406-407]. Pseudohalides include the cyanide ($CN^{-1}$), dicyanimide ($N(CN)_2^{-1}$), thiocyanate ($SCN^{-1}$), cyanate ($OCN^{-1}$), fulminate ($CNO^{-1}$), azide ($N_3^{-1}$), tertrachloroaluminate ($AlCl_4^{-1}$) and other haloaluminates, tertrafluoroborate ($BF_4^{-1}$), haloalkylborates, bistrifylamide (($CF_3SO_2)_2N^{-1}$), hexafluorophosphate ($PF_6^{-1}$), triflate ($CF_3SO_3^{-1}$), and bistriflamide ($CF_3SO_3^{-1}$) anions. Carboxylate anions that contain 1-6 carbon atoms ($C_1$-$C_6$ carboxylate) and are illustrated by formate, acetate, propionate, butyrate, hexanoate, maleate, fumarate, oxalate, lactate, pyruvate and the like. An inionic liquid is hydrophilic and therefore differs from the hydrophobic ionic liquids described in Koch et al. U.S. Pat. No. 5,827,602 or those of Bonhote et al. U.S. Pat. No. 5,683,832 that contain one or more fluorine atoms covalently bonded to a carbon atom as in a trifluoromethanesulfonate or trifluoroacetate anion.

It is preferred that all R groups that are not required for cation formation; i.e., those other than $R^1$ and $R^2$ for compounds other than the imidazolium, pyrazolium and triazolium cations shown above, be hydrido.

A cation that contains a single five-membered ring that is free of fusion to other ring structures is more preferred. Exemplary cations are illustrated below wherein $R^1$, $R^2$, and $R^3$-$R^5$, when present, are as defined before.

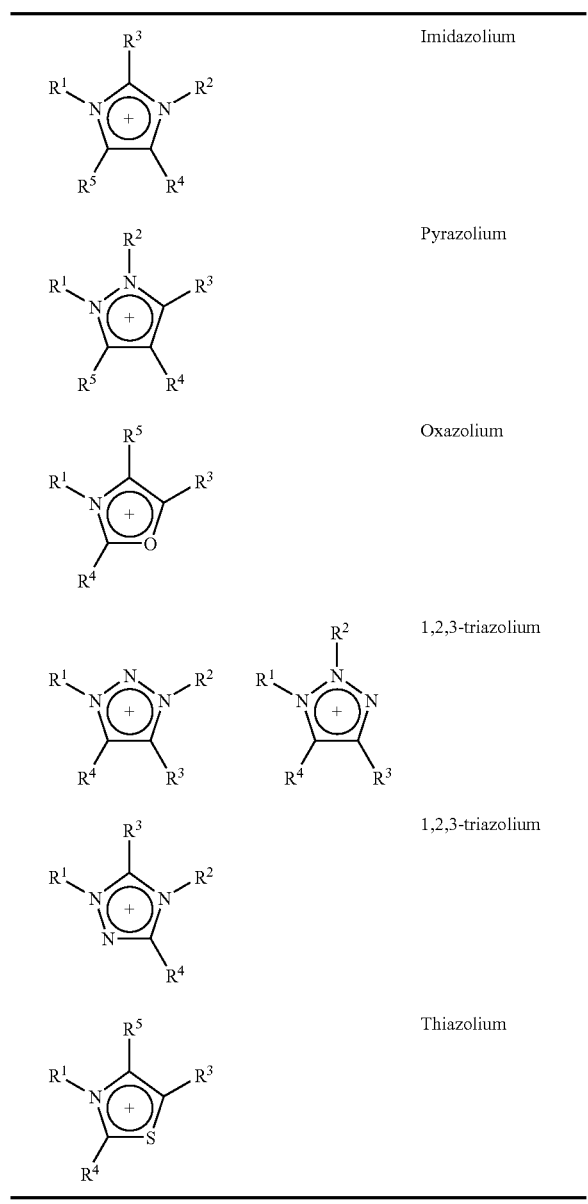

Another aspect of the invention discloses a method for dissolving silk that comprises the steps of admixing silk with a molten ionic to form an admixture. Here the ionic liquid is comprised of cations that contain a single five-membered ring that is free of fusion to other ring structures and anions. The resulting admixture is agitated until dissolution is complete. The admixture can be heated as discussed elsewhere herein to assist the dissolution.

Of the more preferred cations that contain a single five-membered ring free of fusion to other ring structures, an imidazolium cation that corresponds in structure to Formula A is particularly preferred, wherein $R^1$-$R^5$ are as defined before but with the exception that $R^3$ can be a methyl or a hydrido. The anion of the ionic liquid is a halogen or pseudohalogen.

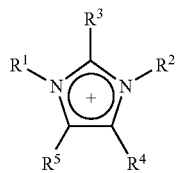

A 1,3-di-($C_1$-$C_6$ alkyl)-substituted-imidazolium and 1,2,3-tri-($C_{1-6}$ alkyl)-substituted-imidazolium ions are more particularly preferred cations; i.e., an imidazolium cation wherein $R^4$-$R^5$ of Formula A are each hydrido, $R^3$ is either a hydrido or a $C_1$-$C_6$-alkyl group or a $C_1$-$C_6$ alkoxyalkyl group, and $R^1$ and $R^2$ are independently each a $C_1$-$C_6$-alkyl group or a $C_1$-$C_6$ alkoxyalkyl group. More preferably still, one of the $R^1$ or $R^2$ groups is methyl and $R^2$ is either a methyl or hydrido. An anion of the ionic liquid whose cation corresponds in structure to a cation of Formula A is a halogen or pseudohalogen.

1-($C_1$-$C_6$-alkyl)-3-(methyl)-imidazolium [$C_n$-mim, where n=1-6] and 1-($C_1$-$C_6$-alkyl)-2,3-dimethyl-imidazolium [$C_n$-dmim, where n=1-6] cations are most preferred, and a halogen is a most preferred anion. A most preferred cation is illustrated by a compound that corresponds in structure to Formula B, below, wherein $R^4$-$R^5$ of Formula A are each hydrido, $R^3$ is a methyl or hydrido, and $R^1$ is a $C_1$-$C_6$-alkyl group. A most preferred anion is a chloride ion.

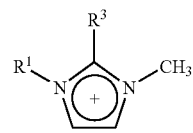

B

A suitable ionic liquid is liquid at or below a temperature of about 200° C., and preferably below a temperature of about 150° C. and above a temperature of about −100° C. For example, N-alkylisoquinolinium and N-alkylquinolinium halide salts have melting points of less than about 150° C. The melting point of N-methylisoquinolinium chloride is 183° C., and N-ethylquinolinium iodide has a melting point of 158° C. More preferably, a suitable ionic liquid is liquid (molten) at or below a temperature of about 120° C. and above a temperature of minus 44° C. (−44° C.). Most preferably, a suitable ionic liquid is liquid (molten) at a temperature of about −10° C. to about 100° C. Silk can be dissolved in high concentration in ionic liquids by heating to about 100° C.

A suitable ionic liquid has an extremely low vapor pressure and typically decomposes prior to boiling. Exemplary liquification temperatures [i.e., melting points (MP) and glass transition temperatures ($T_g$)] and decomposition temperatures for illustrative 1,3-di-$C_1$-$C_6$-alkyl imidazolium and 1,2,3-tri-$C_1$-$C_6$-alkyl imidazolium ion-containing ionic liquids wherein one of $R^1$ and $R^2$ is methyl are shown in the table below.

| Ionic Liquid | Liquification Temperature (° C.) | Decomposition Temperature (° C.) | Citation |
|---|---|---|---|
| [$C_2$mim]Cl | | 285 | a |
| [$C_3$mim]Cl | | 282 | a |

-continued

| Ionic Liquid | Liquification Temperature (° C.) | Decomposition Temperature (° C.) | Citation |
|---|---|---|---|
| [C$_4$mim]Cl | 41 | 254 | b |
| [C$_6$mim]Cl | −69 | 253 | c |
| [C$_8$mim]Cl | −73 | 243 | c |
| [C$_2$mim]I | | 303 | a |
| [C$_4$mim]I | −72 | 265 | b |
| [C$_4$mim] [PF$_6$] | 10 | 349 | b |
| [C$_2$mim] [PF$_6$] | 58-60 | 375 | d, a |
| [C$_3$mim] [PF$_6$] | 40 | 335 | a |
| [iC$_3$mim] [PF$_6$] | 102 | | a |
| [C$_6$mim] [PF$_6$] | −61 | 417 | c |
| [C$_4$mim] [BF$_4$] | −81 | 403, 360 | e, f |
| [C$_2$mim] [BF$_4$] | | 412 | a |
| [C$_2$mim] [C$_2$H$_3$O$_2$] | 45 | | d |
| [C$_2$mim] [C$_2$F$_3$O$_2$] | 14 | About 150 | g |
| [C$_4$mim]Cl | 99 | 150 | h | a Ngo et al., Thermochim. Acta, 2000, 357, 97.
b Fannin et al., J. Phys. Chem., 1984, 88, 2614.
c Swatloski et al., U.S. Pat. No. 6,824,599.
d Wilkes et al., Chem. Commun., 1992, 965.
e Suarez et al., J. Chim. Phys., 1998, 95, 1626.
f Holbrey et al., J. Chem. Soc., Dalton Trans., 1999, 2133.
g Bonhote et al., Inorg. Chem., 1996, 35, 1168.
h MSDS for CAS No. 98892-75-2; Merck KGaA: Darmstadt, Germany, Feb. 22, 2005.

Illustrative 1-butyl-3-methyl-imidazolium ionic liquids, [C$_4$-mim]X [X=Cl$^-$, Br$^-$, I$^-$, BF$_4^-$, and AlCl$_4^-$] have been prepared, as have the ionic liquids 1-ethyl-3-methyl-imidazolium chloride [C$_2$-mim]Cl and 1-butyl-2,3-dimethyl-imidazolium chloride [C$_4$-dmim]Cl. The dissolution of silk in those illustrative ionic liquids under ambient conditions and with heating to 100° C. and with microwave heating has been examined. Silk solutions can be prepared very quickly, which is energy efficient and provides associated economic benefits.

The silk to be dissolved can be in any form that can be mixed with a molten ionic liquid. Exemplary forms of silk used here are derived from Bombyx mori silk and include dry cocoons with sericin, dry cocoons with the sericin removed, silk thread from a commercial source, and recycled silk. Other forms of silk are from synthetic, recombinant proteins, such as silk-elastin like proteins, 15mer spider clones, and CRGD 15mer spider clones.

Silk displays a high solubility in ionic liquids. Viscous, birefringent liquid crystalline solutions are obtained at high concentration, e.g. about 10 to about 25 weight percent. Higher concentrations are possible, but mixing becomes an issue due to the viscosity.

Ionic liquids containing chloride anions appear to be most effective. Other anions, such as Br and I$^-$, would only dissolve the sericin coating on silk cocoons. The BF$_4^-$, and AlCl$_4^-$ anions would dissolve neither the silk or the sericin.

Silk can be regenerated by admixing (contacting) the ionic liquid solution with a non-solvent for the silk that is miscible with the ionic liquid. The non-solvent is preferably miscible with water. Exemplary liquid non-solvents include water, an alcohol such as methanol or ethanol, acetonitrile, an ether such as furan or dioxane, and a ketone such as acetone. Some nonsolvents, such as alcohols, produce silk with a β-sheet crystal structure. Other nonsolvents, such as acetonitrile, produce silk with little β-sheet crystallinity. The advantage of water is that the process avoids the use of a volatile organic compound (VOC), however regenerated, noncrystalline silk is soluble in pure water. Regeneration does not require the use of volatile organic solvents, as sheared silk solutions will form crystalline silk that is not water soluble. The ionic liquid can be dried and reused after regeneration.

Silk can be regenerated from the ionic liquids in a variety of structural forms. These can include flocs or powders (prepared by bulk quenching), tubes, fibers and extrudates, and films. During extrusion, the silk composite can be manipulated to prepare different forms. The regenerated silk appears to be relatively homogenous from scanning electron micrograph (SEM) pictures. In preparing tubes, fibers and other extrudates, the admixing step is carried out by extruding the silk solution through a die or pulling a fiber from bulk into the non-solvent.

Example 1

Silk Dissolution

The cocoon silk utilized in these experiments originated from silkworms raised on a diet of Silkworm Chow (Mulberry Farms, Fallbrook, Calif.). The pupae were extracted from the cocoons intact two to seven days after spinning by cutting open the cocoons. This method avoids possible contamination and thermal degradation from the industrial process of baking the pupae in the cocoons.

For most of the experiments, the sericin was extracted from the silk prior to solubilizing in the ionic liquids. However, for the [C$_4$mim]Br, [C$_4$mim]I, and [C$_4$mim]BF$_4$ experiments, the sericin remained on the fibers, which were dried under vacuum. In the [C$_4$mim]Cl and [C$_4$dmim]Cl experiments, the sericin was stripped in a 0.05M Na$_2$CO$_3$ and 0.05M Na$_2$EDTA solution with 9% (w/w) cocoons at 65° C. for a day. The silk was rinsed thoroughly and lyophilized prior to solubility testing. In the [C$_2$mim]Cl experiments, the sericin was stripped in a 0.2M Na$_2$CO$_3$ solution by boiling for 2 hours. These cocoons were rinsed thoroughly and dried at 100° C. in a vacuum oven overnight prior to solubility testing.

The dissolution experiments were conducted under an inert atmosphere of N$_2$ ([C$_4$mim] and [C$_4$dmim]) or He ([C$_2$mim]) due to the hygroscopic nature of the ionic liquids. To determine the solubility of the silk in each of the ionic liquids, silk was added slowly to the ionic liquid melt while providing agitation. The resultant ionic liquid/silk solutions were clear with an amber color and are quite viscous above 10% (w/w).

The temperatures of the ionic liquid solutions were maintained with a temperature-controlled oil bath at 100° C. Silk fibroin was also successfully dissolved in [C$_4$mim]Cl using microwave radiation to heat the solution. The solubility results listed in Table 1 are samples dissolved using an oil bath as the heat source.

TABLE 1

Saturated Solubility by Weight for Silk in Ionic Liquids

| | Anion | | | | |
|---|---|---|---|---|---|
| Cation | Cl$^-$ | Br$^-$ | I$^-$ | BF$_4^-$ | AlCl$_4^-$ |
| [C$_4$mim]$^+$ | 13.2% | 0.7%[†] | 0.2%[†] | 0.0%[†] | N/D |
| [C$_4$dmim]$^+$ | 8.3% | N/D | N/D | N/D | N/D |
| [C$_2$mim]$^+$ | 23.3% | N/D | N/D | 0.0% | 0.0%[‡] |

[†]Both sericin and fibroin added to the solvent; only the sericin is soluble.
With the exception of BF$_4^-$, these solutions are not saturated.
[‡]Solvent is an [C$_2$mim]Cl/[C$_2$mim]AlCl$_4$ mixture with a 1.0:0.7 molar ratio.

The presence of the chloride anion appears to be critical to the ability of the [C$_4$mim], [C$_4$dmim], and [C$_2$mim] ionic liquids to dissolve silk fibroin. This indicates that the anion plays a critical role in disrupting the hydrogen bonding present in the β-sheets. The lack of solubility of silk in the ternary [C₂mim]Cl/[C₂mim]AlCl₄ system further reinforces this observation. The [C₄mim]Br, [C₄mim]I, and [C₄mim]BF₄ were tested with both silk and sericin. Sericin is soluble in [C₄mim]Br and [C₄mim]I, but not in [C₄mim]BF₄.

Example 2

Silk Solution Characterization

Figure 1B:
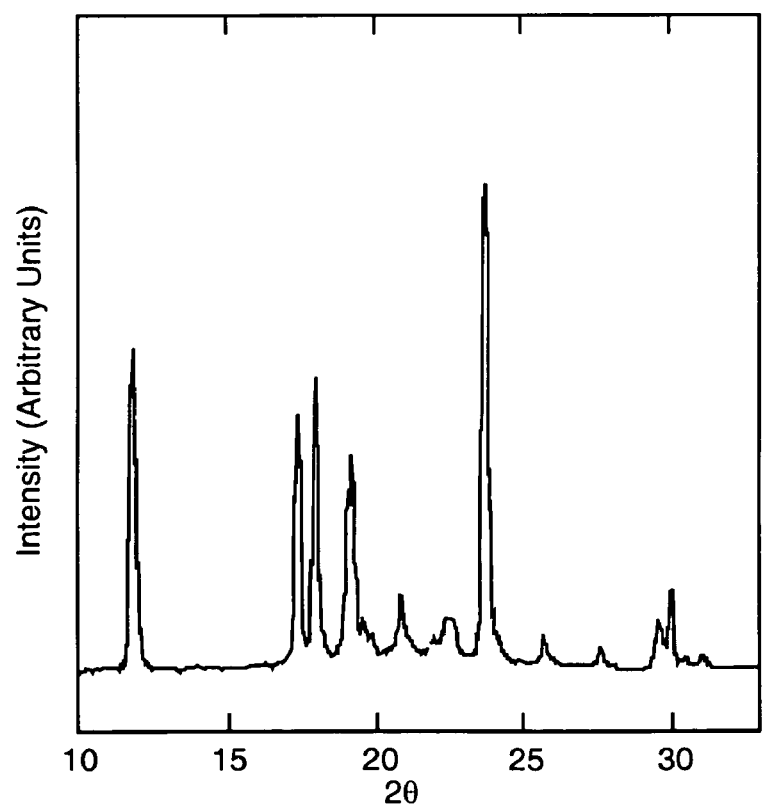

The solubility of the silk fibroin in [C₄mim]Cl was also examined with wide-angle x-ray scattering (WAXS) by examining the crystal structure. As in FIG. 1(a), the data from a 12.24% (w/w) silk solution sealed between Kapton® windows show a peak near a 2θ of 200, indicating amorphous silk, but no β-sheet structure, exists at 30° C. after cooling the solution from 100° C. Furthermore, none of the [C₄mim]Cl peaks are prominent at 30° C. due to the interaction between the [C₄mim]Cl and silk. The pure [C₄mim]Cl data are shown in FIG. 1(b). These data confirm that the [C₄mim]Cl dissolves the cocoon silk by disrupting the hydrogen bonds in the crystalline domains.

Example 3

Silk Regeneration

Figure 2A:
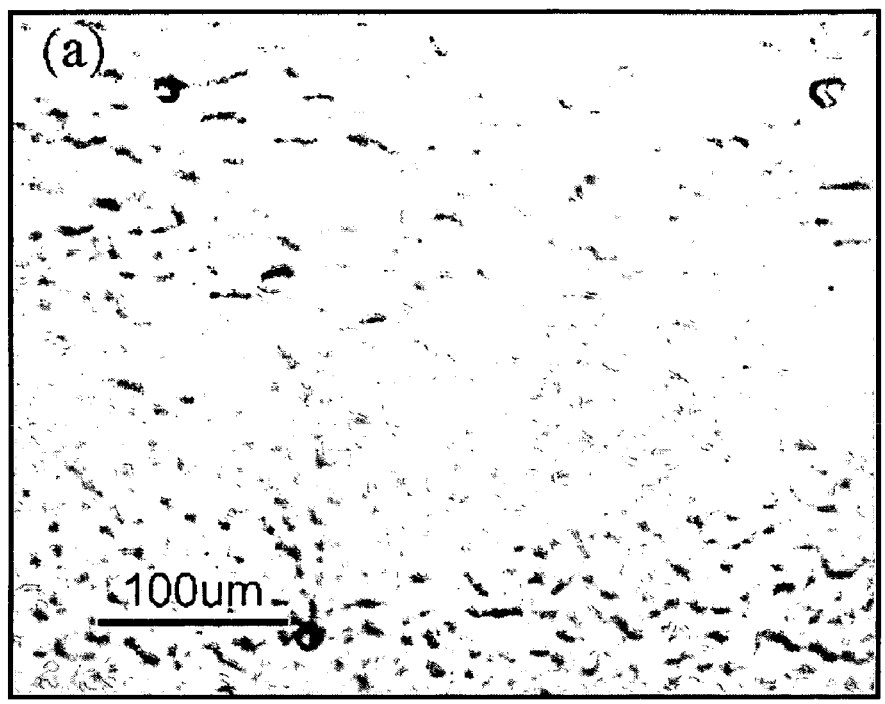
FIGS. 2a and 2b show reflectance optical microscopy images of silk films on glass slides regenerated from 9.51% (w/w) silk in [$C_4$mim]Cl and rinsed with (a) acetonitrile and (b) methanol.
Figure 2B:
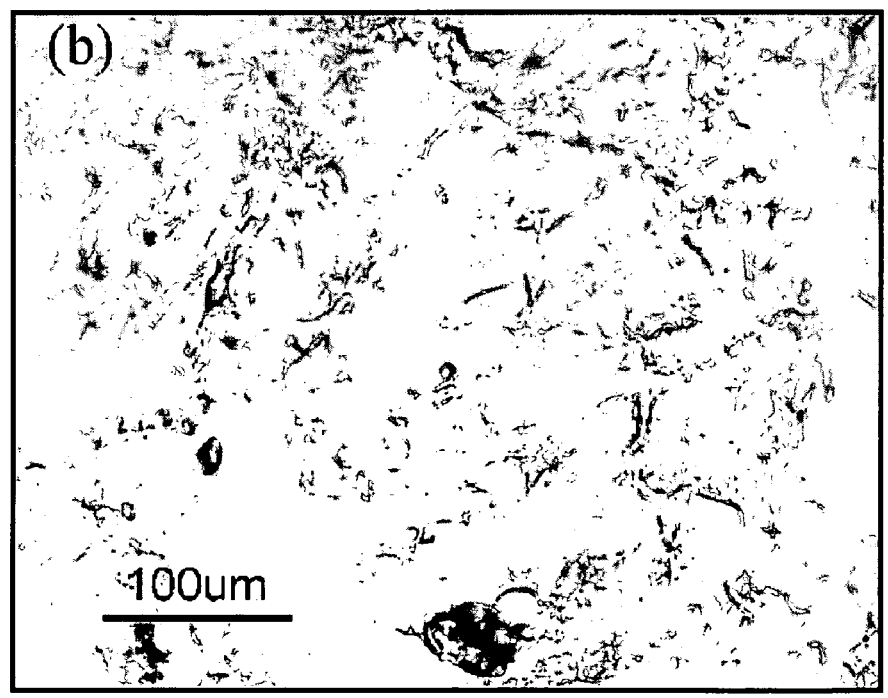

With the solubility of the fibroin firmly established for [C₄mim]Cl, the regeneration of silk from solution was examined. Silk films with ~100 μm thickness were cast onto both glass slides and Si wafers from a 9.51% (w/w) silk in [C₄mim]Cl solution at 100° C. The [C₄mim]Cl was removed by rinsing with either acetonitrile or methanol. Raman analysis indicated that both the acetonitrile and methanol rinses removed the [C₄mim]Cl. Attempts to rinse the [C₄mim]Cl with water resulted in dissolution of the silk film. FIG. 2 shows optical microscopy images of silk films. The acetonitrile rinsed film is white in color due to light scattering and has a visible surface topography. The methanol rinsed film is not smooth, but is transparent. This film is birefringent with 50 μm domains, whereas the acetonitrile rinsed film is not birefringent.

Figure 3A:
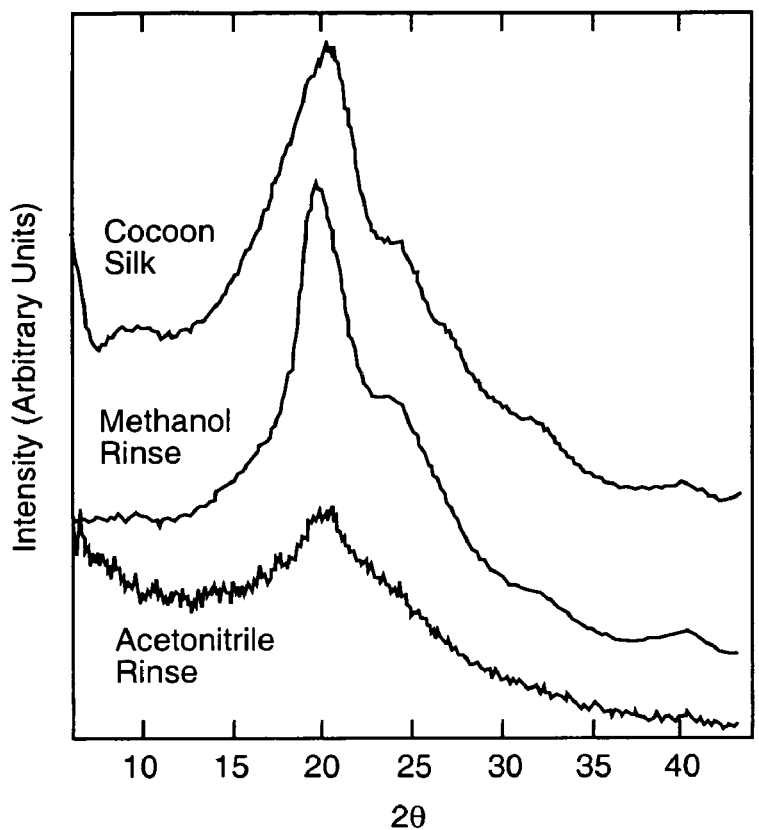
FIG. 3a and 3b is a crystallinity analysis of silk films compared to the natural cocoon fiber.
Figure 3B:
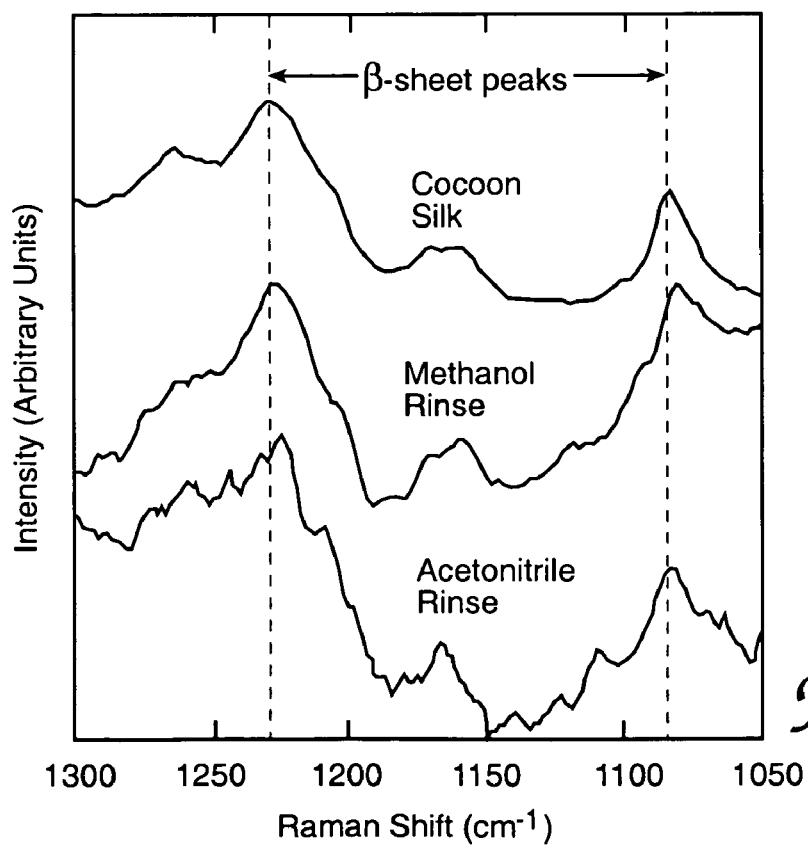

The crystal structure of films cast on silicon wafers were analyzed with both WAXS and laser Raman at 514 nm. FIG. 3 compares both films with a cocoon fiber. FIG. 3(a) shows the WAXS data for the three samples. It is clear that the methanol rinsed film exhibits a high degree of crystallinity that is similar to the cocoon fiber. This is in agreement with previous results that have shown methanol treatment of silk induces the β-sheet structure. In contrast, the acetonitrile rinsed film only has a small degree of crystallinity. The Raman data in FIG. 3(b) indicate that the crystal structure for both films and the cocoon fiber are indeed β-sheet, with peaks at 1229 cm⁻¹ and 1084 cm⁻¹.

What is claimed is:

1. A method for dissolving silk proteins that comprises admixing the silk protein with a molten ionic liquid that has a melting point below about 150° C. to form an admixture, wherein said ionic liquid is comprised of cations and anions.

2. The method according to claim 1 where the silk protein and ionic liquid are combined, heated by conduction, convection, or radiation, including by exposure to microwaves, and agitated until the silk protein dissolves to form an admixture.

3. The method according to claim 2 where the dissolved silk protein is regenerated into solid form by combining the admixture with a hydrophilic nonsolvent liquid for silk protein that leeches the ionic liquid into a phase separate from the solidified silk protein.

4. The method according to claim 3 where the cations of said ionic liquid are selected from the group consisting of

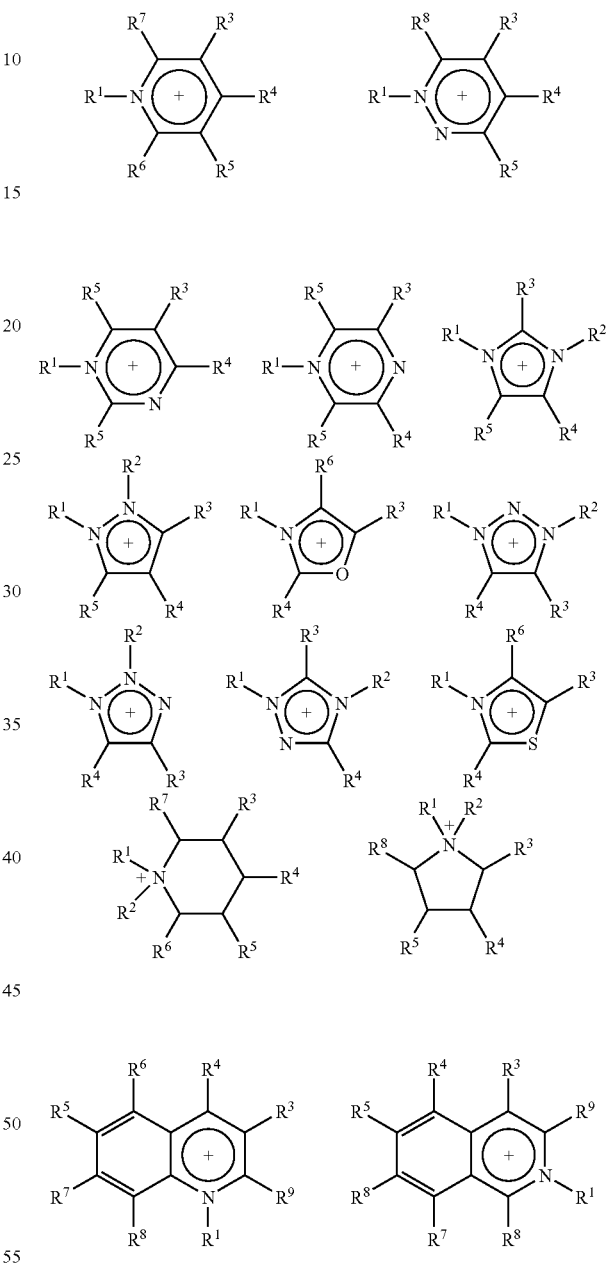

and mixtures thereof, wherein $R_1$ and $R_2$ are independently a $C_1$-$C_6$ alkyl group or a $C_1$-$C_6$ alkoxyalkyl group, and $R_3$, $R_4$, $R_5$, $R_6$, $R_7$, $R_8$, and $R_9$ ($R_3$-$R_9$), when present, are independently a hydrido, a $C_1$-$C_6$ alkyl, a $C_1$-$C_6$ alkoxyalkyl group or a $C_1$-$C_6$ alkoxy group, and the anions of the ionic liquid are halogen, pseudohalogen, or $C_2$-$C_6$ carboxylate.

5. The method according to claim 4 wherein said cation contains a single five-membered ring that is free of fusion to other ring structures and has a structure that corresponds to a formula selected from the group consisting of

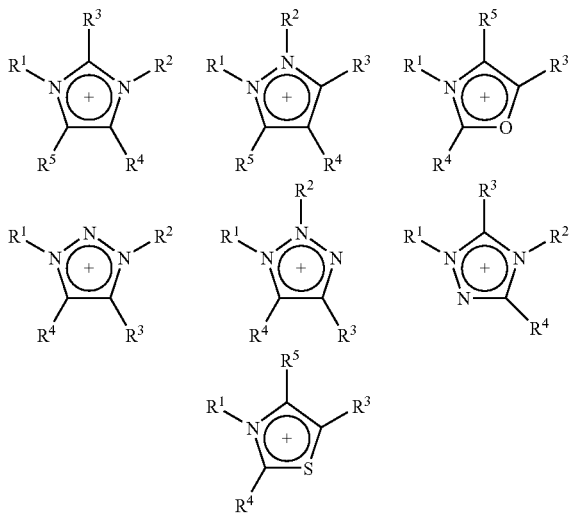

wherein $R^1$ and $R^2$ are independently a $C_1$-$C_6$ alkyl group or a $C_1$-$C_6$ alkoxyalkyl group, and $R^3$, $R^4$, $R^5$ ($R^3$-$R^5$) are independently a hydrido, a $C_1$-$C_6$ alkyl group, a $C_1$-$C_6$ alkoxyalkyl group or a $C_1$-$C_6$ alkoxy group.

6. The method according to claim 5 where $R^4$-$R^5$ are hydrido.

7. The method according to claim 6 where the cation is a 1,3-di-($C_1$-$C_6$-alkyl) imidazolium or 1,2,3-tri-($C_1$-$C_6$-alkyl) imidazolium ion.

8. The method according to claim 7 where the anion is chloride.

9. The method according to claim 8 where the ionic liquid is 1-ethyl-3-methylimidazolium chloride, 1-butyl-3-methylimidazolium chloride, or 1-butyl-2,3-dimethylimidazolium chloride.

10. The method according to claim 3 where the hydrophilic nonsolvent liquid is selected from the group consisting of water, methanol, acetonitrile, and mixtures thereof.

11. The method according to claim 1 wherein said silk protein comprises cocoon silk from the silkworm *Bombyx mori*.

12. The method according to claim 11 wherein said cocoon silk from the silkworm *Bombyx mori* has a sericin coating.

13. The method according to claim 11 wherein said cocoon silk from the silkworm *Bombyx mori* is without a sericin coating.

14. The method according to claim 11 wherein said cocoon silk from the silkworm *Bombyx mori* is obtained from a commercially available silk thread.

15. The method according to claim 11 wherein said cocoon silk from the silkworm *Bombyx mori* is obtained from recycled or discarded silk sources.

16. The method according to claim 1 wherein said ionic liquid is combined with a cosolvent.

17. A method for dissolving synthetic recombinant silk proteins that comprises admixing the synthetic recombinant silk protein with a molten ionic liquid that has a melting point below about 150° C. to form an admixture, wherein said ionic liquid is comprised of cations and anions, and wherein the synthetic recombinant silk protein is selected from the group consisting of silk-elastin proteins and recombinant spider silks.

18. The method according to claim 17 wherein said ionic liquid is combined with a cosolvent.

* * * * *